US009898824B2

(12) United States Patent
Betting et al.

(10) Patent No.: US 9,898,824 B2
(45) Date of Patent: Feb. 20, 2018

(54) METHOD FOR VOLUME EVALUATION OF PENUMBRA MISMATCH IN ACUTE ISCHEMIC STROKE AND SYSTEM THEREFOR

(71) Applicants: SIEMENS HEALTHCARE GMBH, Erlangen (DE); ASSOCIATION POUR LA RECHERCHE EN NEURO-IMAGERIE DE L'HÔPITAL GUI DE CHAULIAC/HOPITAL GUI DE CHAULIAC, Montpellier (FR); CENTRE HOSPITALIER UNIVERSITAIRE DE MONTPELLIER, Montpellier (FR)

(72) Inventors: Fabienne Betting, St Mande (FR); Marion Connan, La Chapelle-Saint-Ursin (FR); Vincent Costalat, Saint Gely (FR); Emmanuelle Le Bars, Prades le Lez (FR)

(73) Assignees: Siemens Healthcare GmbH, Erlangen (DE); Association pour la Recherche en Neuro-Imagerie de L'Hopital Gui de Chauliac/Hopital Gui de Chauliac, Montpellier (FR); Centre Hospitalier Universitaire de Montpellier, Montpellier (FR)

( * ) Notice: Subject to any disclaimer, the term of this patent is extended or adjusted under 35 U.S.C. 154(b) by 132 days.

(21) Appl. No.: 14/833,305

(22) Filed: Aug. 24, 2015

(65) Prior Publication Data
US 2016/0055644 A1    Feb. 25, 2016

(30) Foreign Application Priority Data

Aug. 22, 2014 (EP) .................................. 14290254

(51) Int. Cl.
*G06T 7/00* (2017.01)
*A61B 5/055* (2006.01)
(Continued)

(52) U.S. Cl.
CPC ............ *G06T 7/0081* (2013.01); *A61B 5/055* (2013.01); *G01R 33/5602* (2013.01);
(Continued)

(58) Field of Classification Search
None
See application file for complete search history.

(56) References Cited

U.S. PATENT DOCUMENTS

| 2007/0112264 | A1* | 5/2007 | Wu ....................... A61B 5/0263 600/410 |
| 2009/0034812 | A1* | 2/2009 | Nowinski .............. A61B 5/055 382/131 |
| 2009/0129649 | A1* | 5/2009 | Djeridane ............. G06T 7/0014 382/131 |

(Continued)

OTHER PUBLICATIONS

English Translation of Dumont N. reference cited IDS dated Oct. 13, 2015.*
(Continued)

*Primary Examiner* — Utpal Shah
(74) *Attorney, Agent, or Firm* — Laurence A. Greenberg; Werner H. Stemer; Ralph E. Locher (57) ABSTRACT

A method and a system automatically evaluate the volume of penumbra mismatch during an exam. The method includes performing a magnetic resonance (MR) diffusion-weighted imaging of the brain for acquiring native diffusion images of brain slices. A MR perfusion-weighted imaging of the brain is performed for acquiring native perfusion images of the brain slices. For each brain slice, b0 native diffusion image of the brain slice are segmented to create a contour mask. For each brain slice, a necrosis and cerebrospinal fluid mask (hereafter NC mask) is created from an ADC map of the brain slice. The contour mask and the NC mask of a same
(Continued)

slice are fused. For each brain slice, all native perfusion images acquired for the slice are aligned with the NC mask obtained for the slice and the NC mask is fused with each native perfusion image for obtaining a perfusion image.

8 Claims, 3 Drawing Sheets

(51) Int. Cl.
 G01R 33/56 (2006.01)
 G06T 11/00 (2006.01)
 G06T 7/11 (2017.01)
 G06T 7/12 (2017.01)
(52) U.S. Cl.
 CPC ........ *G01R 33/5608* (2013.01); *G06T 7/0012* (2013.01); *G06T 7/11* (2017.01); *G06T 7/12* (2017.01); *G06T 11/003* (2013.01); *G06T 2207/10072* (2013.01); *G06T 2207/10088* (2013.01); *G06T 2207/30016* (2013.01)

(56) References Cited

U.S. PATENT DOCUMENTS

2013/0144154 A1* 6/2013 Villringer .......... G01R 33/4806
 600/410
2013/0266197 A1 10/2013 Nagenthiraja et al.

OTHER PUBLICATIONS

Dumont N.; "Logiciel D'Estimation de la Zone en Souffrance Pendant Les Accidents Vasculaires Cerebraux"; URL: http://copocorp.free.fr/stage/2011%20-%20Siemene%20-%20ESIEA%20+%20master/Presentation/Presentation%20-%20Courte.pdf; pp. 1-39; XP055157296 / Dec. 5, 2011 [retrieved on Dec. 8, 2014]—Statement of Relevance.
Wikipedia; "Self-organizing map"; Wikipedia, the free encyclopedia; URL: http://en.wikipedia.org/w/index.php?title=Self-organizing map&oldid=611895125; pp. 1-8; XP055157335 / Jun. 7, 2014 [retrieved on Dec. 8, 2014].
Wikipedia; "k-means clustering"; Wikipedia, the free encyclopedia; URL: http://en.wikipedia.org/w/index.php?title=K-means_clustering&oldid=621639177; pp. 1-12; XP055157330 / Aug. 17, 2014 [retrieved Dec. 8, 2014].

* cited by examiner

METHOD FOR VOLUME EVALUATION OF PENUMBRA MISMATCH IN ACUTE ISCHEMIC STROKE AND SYSTEM THEREFOR

CROSS-REFERENCE TO RELATED APPLICATION

This application claims the priority, under 35 U.S.C. § 119, of German application EP 14290254.3, filed Aug. 22, 2014; the prior application is herewith incorporated by reference in its entirety.

BACKGROUND OF THE INVENTION

Field of the Invention

The present invention concerns a method and a system for imaging ischemic stroke in order to help in treatment decision taking.

Ischemic stroke (IS) is caused by a brain vessel occlusion which induces an interruption of the blood flow in the areas normally irrigated by those vessels. Blood flow decrease is responsible for a "time dependent" growing brain infarction area. Without treatment during the three hours following the IS, it might lead to death or handicap, especially when large vessel occlusions are concerned. However, the treatment can generate lethal bleeding and, when ischemia is already in place, it is inefficient. Therefore, it is absolutely crucial to have a tool able to predict the treatment benefit.

Prior art methods used for analysis of diffusion/perfusion magnetic resonance imaging (MRI) brain data consist in computing four different maps. Each one is based on some characteristics of the perfusion signal: cerebral blood flow (CBF), blood volume (CBV), mean transit time (MTT) and time to peak (TTP). Then the operator simply defines manually some areas of interest. In order to decide for the appropriate treatment, the neuroradiologist has to interpret separately each of these maps and then mentally combine them to interpret the series. This work is time consuming while the neuroradiologist is typically dealing with an emergency situation. It also requires a high level of expertise and, in practice, the existing commercial solutions do not provide any automatic clear segmentation of MRI brain images.

SUMMARY OF THE INVENTION

An objective of the present invention is thus to provide a method and system for obtaining a unique and clear segmentation of a diffusion/perfusion MRI brain data in several areas, each one representing a part of the brain, notably healthy parenchyma, necrosis, penumbra, cerebrospinal fluid, and cortical cortex in order to take treatment decision in a faster and more accurate way. Preferentially, the obtaining of the unique and clear segmentation is performed automatically.

This objective is achieved according to the present invention with respect to a method for locating and segmenting ischemic brain penumbra notably after acute ischemic stroke and for evaluating the volume of penumbra mismatch in a brain after the acute ischemic stroke and during an exam of the brain by a magnetic resonance (MR) imaging system. The method is implemented by a system containing at least one processor and one database and that might cooperate with or be part of the MRI system. The method according to the invention includes the below described steps.

a) Perform, by the MR imaging system, MR diffusion-weighted imaging (DWI) of the brain for acquiring b0 and b1000 native diffusion images of slices of the brain and create an apparent diffusion coefficient (ADC) map of each of the slices of the brain. Preferentially, the b0 and b1000 native diffusion images and the ADC maps are stored in a database of the system according to the invention that contains communication devices for communicating with the MRI system in order to exchange/acquire some data, notably the native diffusion images.

b) Perform, by means of the MR imaging system, MR perfusion-weighted imaging (PWI) of the brain for acquiring native perfusion images of the slices of the brain, wherein for instance a contrast agent such as gadolinium might be used for MR PWI, and wherein for each slice, several native per-fusion images are successively acquired during successive acquisition periods. Preferentially, the system according to the invention uses the communication devices for communicating with the MRI system and collecting/acquiring the native perfusion images that might be stored then in the database.

c) For each slice of the brain, the b0 native diffusion image of the slice of the brain is segmented in order to create a contour mask. The contour mask is a mask of the contour of the parenchyma appearing in the b0 native diffusion image of the slice of the brain. The contour mask containing two segments (or groups of voxels), a first segment whose voxels are assigned to a first label or value (the first value being typically equal to 1) and a second segment whose voxels are assigned to a second label or value (the second value being typically 0), so that the mask contains only two labels or values (typically respectively 1 and 0, so that the mask is a black and white image, wherein the white part corresponds to the parenchyma and the black part to parts of the brain other than parenchyma), which advantageously allows to remove from a perfusion image (notably a native perfusion image) unwanted objects such as the eye or artefacts when the contour mask is applied to the perfusion image, notably to a native perfusion image. In particular, mathematical morphology techniques might be used to improve the contour mask. Preferentially, the system according to the invention contains a computer program for automatically performing step (c) and storing each contour mask in the database.

d) For each slice of the brain, a "necrosis and cerebrospinal fluid" mask (hereafter NC mask) is created from the ADC map of the brain slice. The NC mask being configured for eliminating from a native perfusion image of the slice voxels that are not parenchyma, i.e. parts of the native perfusion image representing e.g. noise and cerebrospinal fluid. Preferentially, each NC mask is obtained by segmenting the ADC map in three segments, a first segment whose voxels are assigned to the first label or value (the first value being typically equal to 1) and which represent cerebrospinal fluid, a second segment whose voxels are assigned to the second label or value (the second value being typically 0) and which represents parenchyma, and a third segment whose voxels are assigned to a third label or third value (the third value being comprised between 0 and 1, typically 0.5, so that it becomes possible to differentiate in the NC mask the necrosis, from parenchyma and from cerebrospinal fluid) and which represents the necrosis. For this purpose, the segmentation is preferentially realized by automatically selecting in the ADC map voxels that represent necrosis and assigning the third label to the voxels, wherein the selection is done by determining a first ADC value t1 (hereafter an ADC value is also called intensity value by reference of the intensity of voxels in the ADC map, wherein the intensity of each voxel reflects an estimate of the rate of diffusion at the voxel location) and automatically selecting in the ADC map voxels whose intensity is smaller than t1. The value of t1 being for instance automatically determined by the system according to the invention from histograms of voxel intensity values in each ADC map or chosen by an operator for highlighting in the ADC map the necrosis core. In the ADC map, voxels representing the cerebrospinal fluid are selected and the first label to the voxels is assigned. The selection is done by determining a second intensity value t2 (or ADC value t2) and by automatically selecting in the ADC map voxels whose intensity is greater than t2. Wherein t2 is for instance automatically determined by the system according to the invention from histograms of voxel intensity values in each ADC map or chosen by an operator for highlighting in the ADC map the cerebrospinal fluid, and the second label is assigned to the voxels whose intensity is comprised between t1 and t2, i.e. the second label being assigned in particular to the voxels which have not been previously selected, the voxels representing the parenchyma.

Voxel ADC values for necrosis are typically comprised within the range $[0.2\text{-}0.5] \cdot 10^{-3}$ mm$^2$/s of intensity values and voxel ADC values for healthy parenchyma are typically comprised within the range $[0.7\text{-}0.8] \cdot 10^{-3}$ mm$^2$/s. Preferentially, mathematical morphology techniques might be used to improve the NC mask. The segmentation of the ADC map advantageously allows to highlight the necrosis in the ADC map.

Advantageously, the NC mask is in particular configured for excluding from native perfusion image of the brain slice artefacts (i.e. voxels that aren't body parts) and some specific undesired brain parts like the cerebrospinal fluid so that the unmodified voxels of the image of the slice obtained after applying the NC mask to the native perfusion image are only voxels related to the parenchyma. Typically a NC mask according to the invention is a black and white image containing at least another color and that is of the same dimension of the image of interest (here the native perfusion image), wherein the another color is different from black and white (i.e. a voxel value different from 1 or 0, typically 0.5) and represents the necrosis, wherein each voxel in the NC mask has therefore either a value of 0 (black), 1 (white), or an additional value, typically 0.5, for the another color representing the necrosis. When applying the NC mask to the native perfusion image, the mask and the native perfusion image are merged, and consequently, only the voxels of the native perfusion image corresponding to white parts of the mask will be taken into account for further processing/analysis (they keep their initial intensity value) according to the present invention, while the other voxels, e.g. those corresponding to black parts in the mask, will not be considered for further analysis/processing, i.e. will be ignored for further analysis/processing. Masks according to the present invention allow to determine which voxels have to be taken into account for further processing by determining the areas that are relevant for analyzing the penumbra in brain slice images. The technique of applying a mask to an image for identifying in the image some specific parts/areas is a well-known technique in image processing that does not need a further description. Preferentially, the computer program of the system according to the invention contains code for automatically performing step (d) and storing each NC mask in the database.

e) The contour mask and the NC mask of a same slice are merged for improving the NC mask and using the improved NC mask in the following steps described hereafter. Preferentially, the computer program of the system according to the invention contains code for automatically selecting from the database the contour mask and the NC mask of a same slice and for automatically merging the contour mask and the NC mask according to step (e) in order to obtain for each slice the improved NC mask.

f) For each slice, all native perfusion images acquired for the slice are aligned with the NC mask obtained for the slice so that the head axis in the native perfusion images of the slice becomes aligned with the head axis in the NC mask, and then fusing the NC mask with each native perfusion image for excluding from each native perfusion image of the slice voxels that are not parenchyma. The image obtained after fusing the NC mask with the native perfusion image will be called the improved perfusion image. This process advantageously allows to keep in the resulting native perfusion images, i.e. the improved perfusion images, only voxels that are parenchyma while keeping also information regarding the position of the necrosis. In particular, medical image registration might be used for aligning, for each slice, the head axis in each native perfusion image of the slice with the head axis in the NC mask obtained for the slice. In particular, a b1000 native diffusion image acquired during an acquisition period for one of the slices of the brain might be used as reference for aligning with the NC mask obtained for the one of the slices all native perfusion images acquired during other acquisition periods for the one of the slices, since once the head axis of the b1000 native diffusion image and the head axis of the native perfusion images are aligned, then the native perfusion images become also aligned with the NC mask for the slice. Preferentially, the first native perfusion image acquired during the first acquisition period for each of the slices, i.e. the native perfusion image acquired first by the MRI system for a slice, is first aligned with the NC mask and alignment parameters corresponding to the alignment are calculated, and then the alignment parameters are directly and automatically applied to the other native perfusion images acquired during subsequent acquisition periods (i.e. the native perfusion images acquired temporally after the first native perfusion image during the subsequent acquisition periods) in order to align them with the NC mask. Optionally, the NC mask obtained for a slice might be used as a reference for aligning the native perfusion images of the slice instead of the b1000 native diffusion image, the previously described alignment process for the b1000 native diffusion image being mutatis mutandis used with the NC mask so that the head axis of the NC mask and of the native perfusion images are at the end aligned in the same direction. Advantageously, the alignment of the head axis of the native perfusion images allows to correct patient motion that might occur during the acquisition of native perfusion images. Preferentially, the computer program according to the invention contains code for automatically performing step (f).

g) Preferentially, the position of the necrosis from the NC masks or from the improved perfusion images is determined. Advantageously, since each NC mask contains different labels for respectively the necrosis, the parenchyma and the remaining voxels, it is then easy to determine the position and center of the necrosis since it is characterized by a specific label. In particular, the present invention includes selecting in the improved perfusion image a starting voxel, the starting voxel being located inside the necrosis, preferentially at the center of the necrosis, and being thus a voxel of the necrosis. The alignment and merging of the NC mask obtained for each slice with each of the native perfusion images obtained for each of the slices as described in the previous step (f) allows to precisely locate the necrosis in the improved perfusion images. Preferentially, the starting voxel is the voxel located at the center of the smallest sphere inside which the necrosis is completely inscribed. Preferentially, the computer program according to the invention includes code for automatically performing step (g).

h) A random selection of N perfusion voxels whose positions are outside of the necrosis notably in the improved perfusion images is performed, wherein N is smaller or equal to the total amount M of perfusion voxels acquired during an acquisition period for all the slices, a same number of perfusion voxels being acquired at each acquisition period, and using the improved perfusion images for classifying each randomly selected perfusion voxel whose position is outside the necrosis in a class of voxels among K classes of voxels. In other words, the random selection according to the invention randomly selects perfusion voxels in the three dimensions of the brain images, for example among the improved perfusion images obtained for all slices during one acquisition period, and then classifies the randomly selected perfusion voxels in different classes, notably in function of the evolution of the ADC/intensity value of the voxel in the improved perfusion images acquired during other acquisition periods. For each randomly selected perfusion voxel and thus position within the brain, it is then possible to get the evolution of its ADC and/or intensity value in function of time through the successive periods of acquisition. According to the present invention, the N perfusion voxels are notably chosen outside the necrosis while still being comprised in one of the obtained NC masks. Preferentially, the present invention proposes to use a technique such as the Kohonen self-organization map for classifying each randomly selected perfusion voxel in a class in order to create a topographic map of the brain. In particular, the number K of voxel classes is predefined, e.g. by an operator or in a data file of the MRI system, wherein the random selection of perfusion voxels preferentially starts by randomly selecting perfusion voxels close to the position of the necrosis and continues by selecting perfusion voxels while going away, e.g. continuously or discontinuously going away, from the position of the necrosis, i.e. the distance between the position of the necrosis and the position of the randomly selected perfusion voxels increases during the selection so that the last randomly selected perfusion voxels are the farthest perfusion voxels from the necrosis while the first randomly selected perfusion voxels are the closest ones to the necrosis, and the classification is done in function of the position of the randomly selected perfusion voxel compared to the position of the necrosis and its variation of intensity in function of the time, which is given by measuring the intensity of the randomly selected perfusion voxel at each acquisition period. Indeed, the successive acquisition periods of the native perfusion images provide the temporal evolution of the intensity of each perfusion voxel for each slice. In other words, the successive acquisition periods by means of the MRI system according to the invention allow to acquire successive native perfusion images for each slice providing therefore the variation of intensity of each perfusion voxel in dependence on the time and in particular of the randomly selected voxels. In particular, in order to randomly select perfusion voxels in brain areas under exam while going away from the position of the necrosis, i.e. while increasing little by little the distance between randomly selected perfusion voxels and the position of the necrosis, the present method proposes in particular to define a sphere whose center is the starting voxel and to randomly select perfusion voxels on the surface of the sphere—apart from voxels of the necrosis—while increasing the radius of the sphere, notably until the whole brain is inscribed in the sphere. Preferentially, the method according to the invention uses the K-means clustering method for grouping the randomly selected perfusion voxels, the K-means clustering method comprising measuring for each randomly selected perfusion voxel the variation of its intensity in function of time in order to get for each randomly selected perfusion voxel a signal representing the variation of its intensity in function of the time, filling the K classes with the K first randomly selected perfusion voxels so that each class contains one of the K first randomly selected perfusion voxels, characterizing each class by a mean position and a mean signal that are notably calculated from the improved perfusion images, the mean position being the mean of the positions of the perfusion voxels comprised in the class compared to a coordinate system whose origin is at the center of the necrosis and the mean signal being the mean of the signals representing the variation of intensity in function of the time of the randomly selected perfusion voxels comprised in the class, and classifying iteratively each subsequent randomly selected perfusion voxel according to the following method:

i) comparing the mean position of each of the K classes with the position of the subsequent randomly selected perfusion voxel, and respectively comparing the signal representing the variation of its intensity in function of the time with the mean signal of each of the K classes; and ii) if two classes have mean positions closer to each other than the relative distance separating each of the classes to the position of the subsequent randomly selected perfusion voxel and mean signals more similar with each other than the signal of the subsequent randomly acquired perfusion voxel has compared to the mean signals of each of the classes, then displacing each voxel classified in one of the two classes in the other one so that one of the two classes remains empty, updating the mean position and the mean signal of the class in which the voxels have been displaced, and classifying the subsequent randomly selected perfusion voxel in the other of the two classes, i.e. in the class among the two classes which remained empty after the displacement of the voxels; otherwise iii) classifying the subsequent randomly selected perfusion voxel in the class characterized by a mean position being the closest to the position of the subsequent randomly selected perfusion voxel and by a mean signal being the most similar to the signal of the subsequent randomly selected perfusion voxel. In particular, to determine which mean signal is the most similar to the signal of a subsequent randomly selected perfusion voxel, the present invention proposes to represent the signal and each of the mean signals corresponding to the K classes as Euclidean vectors and to calculate the Euclidean distance between the Euclidean vector of the signal of the subsequent randomly selected perfusion voxel and each of the Euclidean vectors of the mean signals of the K classes, or preferentially those having the closest mean position, e.g. the ten closest mean positions, the class characterized by a mean signal whose Euclidean vector has the smallest Euclidean distance with the Euclidean vector of the subsequent randomly selected perfusion voxel being the class having the mean signal the most similar to the signal of the subsequent randomly selected perfusion voxel. In particular, it is thus possible to classify the classes in function of the similarity of their mean signal with the signal of the subsequent randomly acquired perfusion voxel by measuring the Euclidean distance separating the signal of the subsequent randomly acquired perfusion voxel and the mean signal of each classes, wherein the signal and mean signals are represented as Euclidean vectors; and then:

updating the mean position and the mean signal of the class where the subsequent randomly selected perfusion voxel has been classified.

Preferentially, the computer program according to the invention contains code for automatically performing step (g) and storing in the database data related to the classification of the randomly selected perfusion voxels. In particular, the system according to the invention is able to implement the Kohonen self-organization technique and the K-means clustering method.

i) A map of the brain is created that represents the K classes, the map being in particular a 3-dimensions map. Preferentially, the computer program according to the invention comprises code for automatically performing step (i) from the data stored in the database and in particular for storing the map obtained under step (i) in the database.

j) A final image of the brain is created by grouping in the map of the brain obtained according to step (i) the classes in a predefined number F of families, for instance F equals 2 to 5 families, wherein the number F of families might be chosen by an operator or predefined in the database of the system according to the invention, and wherein at least one family corresponds to penumbra. The final map according to the invention is in particular a 3-dimensions image of the brain. Preferentially, the grouping is done by comparing the mean position and mean signal of the classes, e.g. by using a K-means clustering method, or in particular by merging the classes having the closest mean position together with the most similar mean signal into one family until reaching the predefined number F of families. Preferentially, the computer program according to the invention contains code for automatically performing step (j) and in particular, for storing the final map in the database.

k) The volume of penumbra mismatch is calculated from the final image of the brain, wherein the volume of the penumbra mismatch equals to the sum of the volumes of the voxels belonging to each family corresponding to penumbra. Advantageously, the system according to the invention is able to determine which family corresponds to which part of the brain by calculating the sum of the volumes of the voxels belonging to each family, the largest volume corresponding to healthy parenchyma and the remaining volumes that are connected directly or indirectly by at least one voxel to the necrosis corresponding to penumbra (by connected "indirectly" it is understood that a voxel indirectly connected to the necrosis is connected to a group of voxels wherein each voxel of the group has a connection with at least one other voxel of the group, and that at least one voxel of the group is directly connected to the necrosis). Optionally a family corresponding to necrosis might be determined by the system according to the invention from the knowledge of the position of the necrosis. According to the present invention, penumbra families are in particular characterized by different mean voxel positions and mean signals. Preferentially, the computer program according to the invention comprises code for automatically performing step (j). Preferentially, the system according to the invention is configured for automatically displaying on a display the final map and the calculated volume(s) of penumbra mismatch.

Advantageously, each step of the previously described method might be performed automatically by the system according to the invention in order to automatically obtain a clear segmentation of MRI diffusion/perfusion brain data in several areas, each one representing a part of the brain.

Finally, the present invention also claims a MRI system for carrying out the previously described method and steps.

According to the present invention, diffusion data, e.g. isotropic ADC maps obtained from b0 and b500 to b1000 images, usually b0 and b1000, might be used to segment the necrosis core. Advantageously, segmenting the necrosis core on diffusion data is a reliable way to find necrosis area, which might be then reported on the perfusion data as previously described. Indeed, in perfusion images of prior art techniques, the necrosis core is mostly merged with the penumbra and consequently it becomes difficult to differentiate the necrosis core from the penumbra from perfusion data.

In particular, the parameters that might be used by the system according to the invention for constructing the ADC map from diffusion data and thus obtaining the necrosis segmentation are:

i) the ADC value in each voxel, that might be stored in the database; and ii) the ADC mean value in the necrosis core and in the parenchyma, that might be stored in the database.

Other features which are considered as characteristic for the invention are set forth in the appended claims.

Although the invention is illustrated and described herein as embodied in a method for volume evaluation of penumbra mismatch in acute ischemic stroke and a system therefor, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1A:
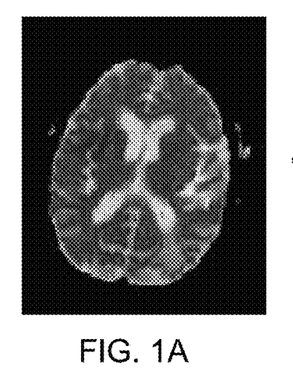
FIG. 1A is a schematic representation of a method according to the invention, which shows an ADC map.
Figure 1B:
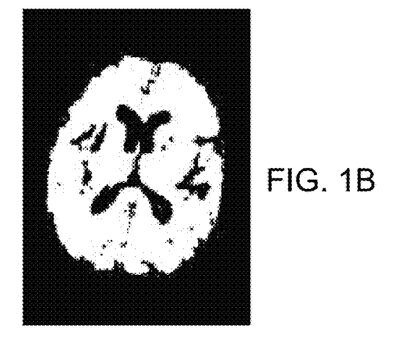
FIG. 1B is a schematic representation showing an improved NC mask.
Figure 1C:
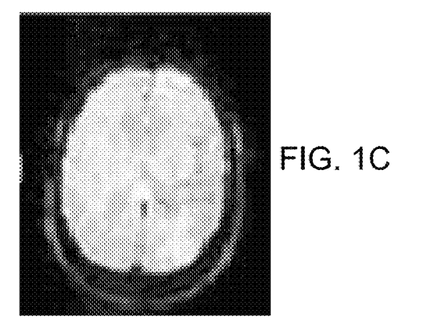
FIG. 1C is a schematic representation showing a native perfusion image.
Figure 1D:
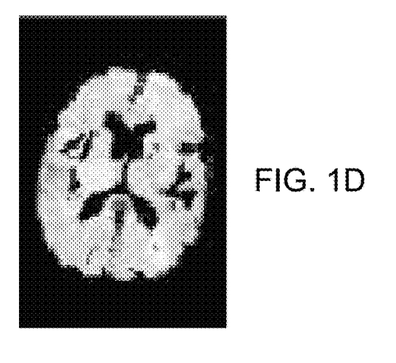
FIG. 1D is a schematic representation showing an improved perfusion image.

Referring now to the figures of the drawings in detail and first, particularly to FIG. 1 thereof, there is shown the present invention which proposes in particular to use an ADC map (see FIG. 1A) in order to create a mask (see the NC mask shown in FIG. 1B). The mask is then fused with a native perfusion image (see FIG. 1C) for creating an improved perfusion image (see FIG. 1D) that is used for segmenting different areas of the brain, notably healthy parenchyma, necrosis, penumbra, cerebrospinal fluid, and cortical cortex in order to take treatment decision in a faster and more accurate way.

Figure 2:
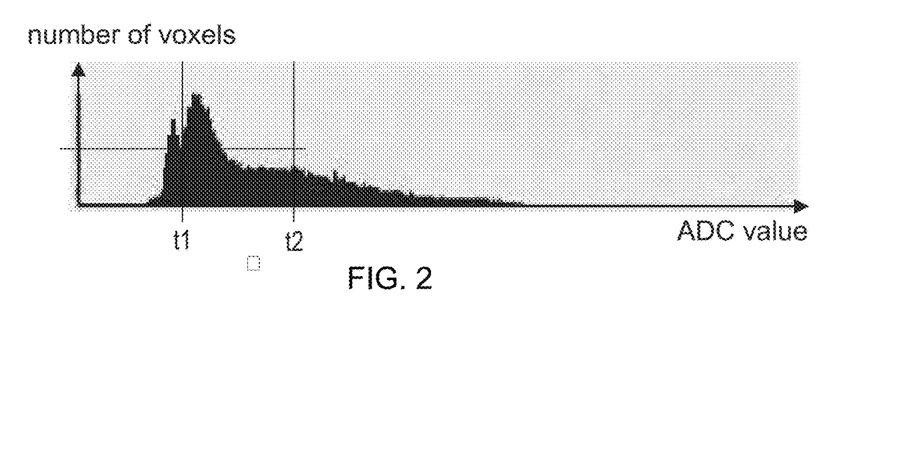
FIG. 2 is a histogram showing a number of diffusion voxels in dependence on the ADC values of voxels in the ADC maps.

According to the present invention, voxels of the ADC map (FIG. 1A) whose ADC value is comprised within a range of intensity values [0, t1] representing necrosis, [t2, ∞] representing cerebrospinal fluid (see FIG. 2) are selected for segmenting the ADC map (see FIG. 2). The intensity value t1 belongs in particular to the range of values $[0.2\text{-}0.5] \cdot 10^{-3}$ mm$^2$/s. Advantageously, the necrosis core has a higher visibility after segmentation of the ADC map compared to its visibility in the ADC map free of segmentation. It becomes thus possible to create a mask, called NC mask, that allows to clearly differentiate in voxels representing necrosis core from voxels representing healthy parenchyma. Indeed, the Applicant has noticed that when making histograms from ADC values of voxels in ADC maps (number of voxels per intensity) (see FIG. 2), a same histogram profile is observed from a patient to another, the profile being characterized by a secondary peak appearing for small ADC values corresponding to necrosis, a main peak followed by a plateau for ADC values corresponding to healthy parenchyma, and from the plateau, a continuous decrease of the number of voxel by increasing the ADC value. Such a histogram is shown in FIG. 2. It shows the secondary peak beside the main peak for smaller ADC values, the secondary peak representing a high concentration of voxels for dark values: it corresponds to the intensities where one can find the necrosis core, while the main peak represents healthy parenchyma with typical ADC values comprised within the interval $[0.7\text{-}0.8] \cdot 10^{-3}$ mm$^2$/s, and higher ADC values comprised in the interval [t2, ∞] represent the cerebrospinal fluid. The thresholds t1, t2, might be in particular tuned by an operator of the MRI system or preferentially automatically determined by the system according to the invention by calculating the number of voxels per ADC values in ADC maps and determining, e.g. from an histogram of ADC values of voxels in ADC maps, the range of ADC values or voxels intensities corresponding to necrosis (e.g. ADC "dark values"), the cerebrospinal fluid and the parenchyma, for instance by fitting such a histogram with a curve and searching for ADC values or voxel intensities of inflexion points in order to determine the position of the first and second peak comprised respectively in the range [0, t1] and [t1, t2] and corresponding respectively to necrosis and healthy parenchyma, and wherein t2 might be determined by fitting the plateau appearing after the second peak corresponding to the healthy parenchyma and determining its end . According to the present invention, the histogram of ADC values of voxels in ADC maps might be used for segmenting the ADC map in the previously described three segments in order to create the NC mask as shown in FIG. 1B.

Preferentially, an algorithm of growing region is used to find edges of the necrosis core in ADC maps before or after their segmentation. In particular, the algorithm is able to find multiple areas of necrosis in the ADC maps by analyzing voxel intensities. In particular, the seed for the origin of the growth is a small amount of voxels in the darken area, which corresponds to the necrosis core. Preferentially, another seed for the origin of another growth is a small amount of voxels having an intensity (or ADC values) corresponding to necrosis (i.e. comprised in the range [0, t1]) and located in another darken area. In other words, by analyzing the position voxels characterized by ADC values corresponding to necrosis, the method according to the invention is able to find different necrosis areas and to characterize the edges of the necrosis by using the algorithm of growing region for each of the necrosis areas. Different seed positions might be thus used. Preferentially, the algorithm of growing region according to the invention is capable of automatically finding multiple positions of necrosis in the improved ADC maps, the multiple positions being used as origin positions for multiple growing regions in order to segment multiple areas of necrosis in the ADC maps.

According to the present invention, perfusion data are used to extract the penumbra by analyzing voxel intensity in native perfusion images. For this purpose, native perfusion images are aligned on the NC mask by preferentially using an algorithm of rigid registration capable of aligning in the same direction the axis of the head appearing in the brain image of NC mask with the axis of the head appearing in the brain image of the native perfusion image. Medical image rigid registration might thus be used for transforming the set of data coming from the NC mask and the set of perfusion data coming from the perfusion image into one coordinate system which is the coordinate system of the NC mask, i.e. the NC mask preferentially serves as reference for aligning the native perfusion images. Medical image registration of two images (presently the NC mask and a native perfusion image), and in particular rigid registration, is well known by the skilled man and does not need further description. Once a native perfusion image is aligned with the NC mask, then they are merged to form the improved perfusion image as presented in FIG. 1D. In the improved perfusion image, the shape of the brain coming from the NC mask and the shape of the brain coming from the native perfusion image are superposed. An advantage of using the NC mask on the native perfusion images is to exclude from each native perfusion image anything that is not parenchyma. Preferentially, the NC mask contains the ventricles and is merged with a contour mask.

Figure 3A:
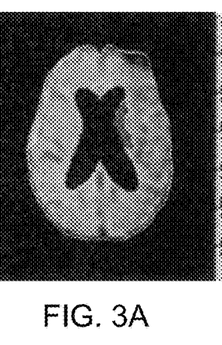
FIG. 3A is a schematic representation of an improved perfusion image according to the invention.

The result of merging a NC mask with a perfusion image is also shown in FIG. 3A, which corresponds to an improved perfusion image. The method according to the invention contains in particular a random selection of perfusion voxels in improved perfusion images corresponding to native perfusion images acquired during a same acquisition period. Since for a same slice, native perfusion images, and consequently improved perfusion images, might be sorted by the system according to the invention according to their time of acquisition by the MRI system, the improved perfusion images comprise the same temporal information of the evolution of perfusion data as the native perfusion images, and by selecting voxels with the same coordinates in the improved perfusion images obtained from successive acquisition of native perfusion images, and measuring the intensity of the voxels, it is possible to get for each voxel a signal of the variation of its intensity in function of the time. Consequently a signal representing the variation of intensity of the voxel during the acquisition of perfusion data might be obtained by the system according to the invention for each voxel and assigned to the voxel: e.g. a signal SL might be assigned to a perfusion voxel VL, wherein the signal SL might be represented as an Euclidean vector whose components SL,i are the intensity values of the voxel VL in function of the time, the intensity being measured through the successively acquired native perfusion images, SL,i being the voxel intensity value in the native perfusion image acquired at the ith acquisition period, and wherein L=1,N. Preferentially, the signals might be represented by smoothed curves or fitted by a curve displaying the components SL,i in function of time and representing the passage of the contrast agent used during the exam, which advantageously allows to associate the signals with characteristic parameters of the cerebral parenchyma perfusion, such as TTP, CBV, MTT, CBF.

Figure 3B:
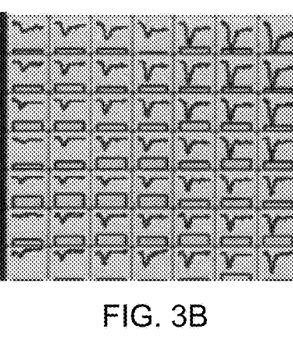
FIG. 3B is a schematic representation of 49 classes according to the invention and issued from the left image.
Figure 3C:
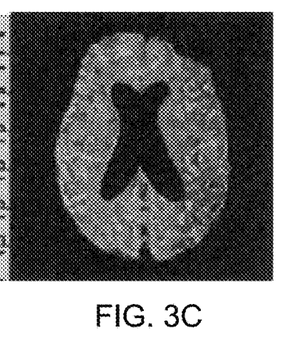
FIG. 3C is a schematic representation of a resulting map of the brain containing ROIs corresponding to the 49 classes of topographic maps.

According to the present invention, the signals of the randomly selected perfusion voxels are preferentially grouped by the system according to the invention in a predefined number of K classes in function of their similarity and the position of the randomly selected perfusion voxel compared to the necrosis. Wherein the number of classes might be defined in function of the shape of the curves of the signals SL. FIG. 3B presents for example a classification of the randomly selected perfusion voxels into K=49 classes in function of their signal and position. Preferentially, each signal is stored as an Euclidean vector SL, wherein each component SL,i of the Euclidean vector SL is an intensity of the randomly selected perfusion voxel in one of the temporally subsequently acquired (improved) perfusion images. In other words, the variation of the intensity in function of time for a position (which is the position of the randomly selected perfusion voxel which remains the same through the successively acquired (improved) perfusion images), is given by the components of SL. Preferentially, the differences or similarities between two signals might then be calculated by the processor of the system according to the invention by using the Euclidean distance (or Euclidean norm). Preferentially, a Kohonen self-organization map might be used by the system according to the invention for classifying the randomly selected perfusion voxels in K classes and for representing a map of the classes as shown in FIG. 3C.

Figure 4A:
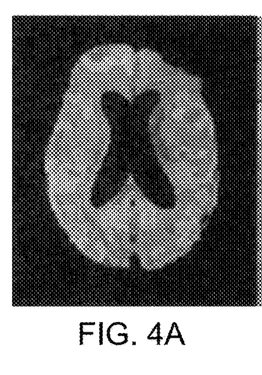
FIG. 4A is a schematic representation of a final image of the brain i.e. a map of the brain after a reduction of the ROI number from 49 classes to 5 families corresponding to cerebral tissue.
Figure 4B:
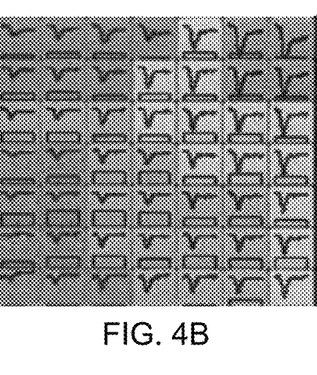
FIG. 4B is a schematic representation of topographic maps issued from the left image.
Figure 4C:
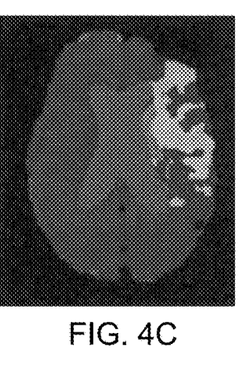
FIG. 4C is a schematic representation of an improved final image according to the invention, wherein a color (or greyscale) palette is applied and the penumbra is discriminated from other tissues.

Once the K classes are determined by the system according to the invention, the present invention proposes in particular to sort the classes into F families (F<K) or Regions of Interest (ROIs) that represent parts and perfusion characteristics of the brain, particularly the penumbra, and to create a final image from the previously obtained map of the brain wherein the families or ROIs are represented. FIGS. 4A-4C presents the clustering of the 49 classes into 5 families corresponding to cerebral tissue (see FIG. 4A), corresponding topographic maps (see FIG. 4B), and the final image wherein the penumbra is clearly segmented from other tissues (see FIG. 4C).

Preferentially, a K-means clustering method is used by the system according to the invention to compare the mean signal of each class and the mean position in order to group the classes in F families. Optionally, each family might be associated to a specific color by the system according to the invention. In particular, a fixed color palette might be set in order to always have the same kind of brain tissues in the same color from a patient to another. The kind of brain tissues (or parts of brain) recognition is in particular based on the size of the family or ROIs (biggest=parenchyma) or the connectivity between each family or ROIs (closest to necrosis=penumbra), wherein the system according to the invention is able to determine that a family corresponds to penumbra if at least one voxel of the family makes a connection between the family and the necrosis.

In summary, the present invention proposes to use two different segmentation algorithms that might be coded in the computer program of the system according to the invention and executed by the system: a first one for thenecrosis segmentation in DWI data and a second one for the penumbra segmentation in PWI data. In particular, the necrosis segmentation according to the invention uses curves or signals representing variation of voxel intensity in function of time, and classes randomly selected voxels in function of their position and the aspect or shape of their signal. Computing characteristic parameters of the cerebral parenchyma perfusion might be done by the system according to the invention in the obtained ROIs for comparing results obtained with the present method with values given in the literature. Preferentially, the claimed method is completely automatic—the steps (a)-(j) being automatically performed, e.g. by the system according to the invention or by equipment comprising the system according to the invention, the steps being performed the one after another without any input from an operator—, while containing or not some steps requiring an input from an operator: for example, an operator may modify the parameters of the method (threshold values t1 and/or t2, the number of ROIs or families, the number of classes, the value of N, etc).

The invention claimed is:

1. A method for automatically locating and segmenting ischemic brain penumbra during an exam of a brain by a magnetic resonance (MR) imaging system and evaluating a volume of penumbra mismatch, which comprises the steps of:

a) performing MR diffusion-weighted imaging (DWI) of the brain for acquiring b0 and b1000 native diffusion images of slices of the brain and creating an apparent diffusion coefficient (ADC) map of each of the slices of the brain;

b) performing MR perfusion-weighted imaging (PWI) of the brain for acquiring native perfusion images of the slices of the brain, wherein for each slice, several of the native perfusion images are successively acquired during successive acquisition periods;

c) for each of the slices of the brain, segmenting the b0 native diffusion image of the slice of the brain to create a contour mask, the contour mask being a mask of a contour of a parenchyma appearing in the b0 native diffusion image of the slice of the brain;

d) for each of the slices of the brain, creating a necrosis and cerebrospinal fluid mask, hereafter NC mask, from the apparent diffusion coefficient (ADC) map of the slice of the brain;

e) fusing the contour mask and the NC mask of a same slice of the brain;

f) for each of the slices of the brain, aligning all the native perfusion images acquired for the slice with the NC mask obtained for the slice so that a head axis in the native perfusion images becomes aligned with a head axis in the NC mask and then fusing the NC mask with each native perfusion image for obtaining an improved perfusion image;

h) randomly selecting N perfusion voxels whose positions are outside of the necrosis, wherein N is smaller or equal to a total amount M of the perfusion voxels acquired during one acquisition period for all the slices, and using improved perfusion images for classifying each randomly selected perfusion voxel in a class of voxels among K classes of voxels, wherein a random selection of the perfusion voxels includes increasing a distance between a randomly selected voxel and the necrosis from first randomly selecting perfusion voxels to a last randomly selecting perfusion voxel;

i) creating a map of the brain that represents the K classes;

j) creating a final image of the brain by grouping in the map of the brain the classes in a predefined number F of families, wherein the family whose voxels represent a largest volume corresponds to a healthy parenchyma, and remaining families which have at least one voxel that is connected directly or indirectly to the necrosis correspond to the penumbra; and k) calculating a volume of the penumbra mismatch from the final image of the brain, wherein the volume of the penumbra mismatch equals to a sum of volumes of the voxels belonging to each family corresponding to the penumbra.

2. The method according to claim 1, which further comprises segmenting the ADC map into three segments, respectively including a first segment representing cerebrospinal fluid, a second segment representing the parenchyma and a third segment representing the necrosis, in order to obtain the NC mask.

3. The method according to claim 2, wherein a segmentation into the three segments is realized by automatically selecting in the ADC map voxels whose intensity values are comprised within a first range of values for the necrosis and a second range of values for the cerebrospinal fluid.

4. The method according to claim 1, which further comprises classifying randomly selected perfusion voxels in the K classes in dependence on their position and a variation of their intensity in dependence on time in the improved perfusion images.

5. The method according to claim 1, wherein a classification of randomly selected voxels into the K classes includes filling the K classes with K first randomly selected perfusion voxels, characterizing each class by a mean position and a mean signal, and classifying iteratively each subsequent randomly selected perfusion voxel according to the following steps:

comparing the mean position of each of the K classes with a position of a subsequent randomly selected perfusion voxel, and respectively comparing a signal representing a variation of its intensity in dependence on time with the mean signal of each of the K classes;

if two classes have mean positions closer to each other than a relative distance separating each of the classes to the position of the subsequent randomly selected perfusion voxel and mean signals more similar with each other than the signal of the subsequent randomly acquired perfusion voxel has compared to the mean signals of each of the classes, then displacing each voxel classified in one of the two classes in the other one so that one of the two classes remains empty, updating the mean position and the mean signal of the class in which the voxels have been displaced, and classifying the subsequent randomly selected perfusion voxel in the other of the two classes;

otherwise classifying the subsequent randomly selected perfusion voxel in the class characterized by the mean position being closest to the position of the subsequent randomly selected perfusion voxel and by the mean signal being a most similar to the signal of the subsequent randomly selected perfusion voxel; and then updating the mean position and the mean signal of the class where the subsequent randomly selected perfusion voxel has been classified.

6. The method according to claim 1, which further comprises a step of (g) determining a position of the necrosis from the NC masks.

7. A system, comprising:

a processor;

a database;

at least one non-transitory computer medium having a computer program for automatically carrying out a method according to claim 1; and a communication device for exchanging data with a magnetic resonance imaging system.

8. A magnetic resonance imaging system, comprising:

a processor;

a database;

at least one non-transitory computer medium having a computer program for automatically carrying out a method according to claim 1; and a communication device for exchanging data throughout the magnetic resonance imaging system.

* * * * *